# (12) United States Patent
Cain et al.

(10) Patent No.: US 7,163,950 B1
(45) Date of Patent: Jan. 16, 2007

(54) SURFACTANTS AS MALARIAL CHLOROGUINE RESISTANCE REVERSAL AGENTS

(75) Inventors: Kevin C. Cain, Toronto (CA); Ian Crandall, North York (CA); Jeffrey Charuk, Toronto (CA); Reinhart Reithmeier, Toronto (CA)

(73) Assignee: University Health Network, Toronto (CA)

( * ) Notice: Subject to any disclaimer, the term of this patent is extended or adjusted under 35 U.S.C. 154(b) by 206 days.

(21) Appl. No.: 10/148,498

(22) PCT Filed: Nov. 28, 2000

(86) PCT No.: PCT/CA00/01400

§ 371 (c)(1),
(2), (4) Date: Oct. 23, 2002

(87) PCT Pub. No.: WO01/39757

PCT Pub. Date: Jun. 7, 2001

(51) Int. Cl.
*A01N 43/42* (2006.01)
*A01N 31/14* (2006.01)
*A01N 37/00* (2006.01)
*A61K 31/08* (2006.01)

(52) U.S. Cl. .................. 514/313; 514/718; 514/723; 514/560

(58) Field of Classification Search ............... 514/313, 514/718, 723, 560
See application file for complete search history.

(56) References Cited

U.S. PATENT DOCUMENTS 5,741,525 A * 4/1998 Larsen .................. 424/616
5,776,891 A * 7/1998 Coon et al. .................. 514/10
6,045,786 A * 4/2000 Cone et al. .............. 424/78.02

OTHER PUBLICATIONS

Merck Index 10th edition, windholz et al Eds. Merck & Co., Rathway N.J. 1983, abstract #6518.*
White et al. "The Treatment of Malaria" 1996, The New England Journal of Medicine, 335(11), 800-6.*
Intestinal Permeability Enhancement: Structure-Activity and Structure-Toxicity Relationships for Nonylphenoxypolyoxyethylene Surfactant Permeability Enhancers. Pharmaceutical Research, vol. 11, No. 10, pp. 1501-1504, 1994.
Crandall, Ian et al. (2000). Nonylphenolethoxylates as Malarial Chloroquine Resistance Reversal Agents. *Antimirobial Agents and Chemotherapy* 44:9 (2431-2434).
International Search Report, Oct. 15, 2001.

* cited by examiner

*Primary Examiner*—Shengjun Wang
*Assistant Examiner*—Yong S. Chong
(74) *Attorney, Agent, or Firm*—Bereskin & Parr

(57) ABSTRACT

According to the first aspect of the invention, a composition for reversing malarial resistance to quinolines is disclosed. The composition includes a surfactant, such as nonylphenolethoxylate (NPE) in an admixture with a pharmaceutically acceptable carrier, excipient, or diluent. According to a second aspect of the invention, a composition for the prevention or treatment of malaria is provided. The composition comprises a pharmaceutically effective amount of a quinoline in combination with a surfactant, such as NPE, for reversing malarial resistance to quinolines. According to a third aspect of the invention, a method of preventing or treating malaria in a person is provided. The method comprises administering to a patient in need thereof one or both of the compositions described above.

16 Claims, 3 Drawing Sheets

SURFACTANTS AS MALARIAL CHLOROGUINE RESISTANCE REVERSAL AGENTS

BACKGROUND OF THE INVENTION

1. Field of the Invention

This invention relates to compositions and methods for preventing or treating *Plasmodium falciparum* malaria. In particular, this invention relates to surfactant compositions and methods for reversing malarial resistance to quinoline antimalarials.

2. Description of the Prior Art

*Plasmodium falciparum* malaria is the world's most important parasitic infection accounting for an estimated 300 to 500 million cases and 1.5 to 2.7 million deaths annually [reviewed in Kain, 1998a]. *P. falciparum* infection accounts for over 90% of the morbidity and mortality associated with malaria. Young children living in malaria-endemic areas and other non-immune individuals are at the greatest risk of developing severe complications such as cerebral malaria leading to death. Despite intensive research, no specific treatments have been identified to prevent or improve the outcome of patients with severe malaria [White, 1998]. Severe and cerebral malaria carries a high fatality rate (>15%) even for young, previously healthy individuals [White 1998]. With escalating drug resistance and the lack of an effective vaccine, there is an urgent need for alternative therapeutic strategies.

Malaria associated morbidity and mortality is increasing because of widespread resistance to chloroquine, which is one of the safest and least expensive antimalarials. Chloroquine-resistant *P. falciparum* malaria was first recognized over 40 years ago and has since spread to almost all malaria-endemic areas [Su, 1997]. Chloroquine-resistant malaria has extended into the high transmission areas of Africa resulting in a public health crisis since switching to alternative antimalarials, such as mefloquine, artemisinin derivatives, halofantrine or quinine, is economically untenable for many countries in sub-Saharan Africa. Recent reports indicate that escalating mortality due to widespread malaria resistance is now taking place [Marsh, 1998].

The mechanism of chloroquine-resistance in *P. falciparum* remains controversial. However, it is frequently compared to multidrug resistance in mammalian cells that is often mediated by P-glycoproteins [Bray, 1998]. Mammalian P-glycoproteins are intrinsic membrane protein drug transporters that actively pump a wide variety of drugs and other xenobiotic compounds out of cells. Although P-glycoproteins can pump many types of chemotherapeutic agents like vinblastine and adriamycin out of cancer cells, the multidrug resistance phenotype of such cells can be modified by a variety of compounds including the immunosuppressant, cyclosporin A and calcium channel blockers such as verapamil. These chemosensitizers, competitively interact with drug-binding sites on P-glycoprotein, thereby interfering with the transport of chemotherapeutic agents out of cells.

It is known that drug resistance in *P. falciparum* can be reversed by calcium channel blockers such as verapamil [Martin. 1987]. The antipsychotics (e.g. chlorpromazine [Basco. 1992]), and histamine (H-1) receptor antagonists (e.g. promethazine [Oduola. 1998], chlorpheniramine [Basco, 1994]) also reverse chloroquine-resistance in *P. falciparum* in vitro and in malaria animal models [Bray. 1998]. However, these agents are pharmacologically active compounds with multisystem effects that result in a variety of undesirable side effects. Furthermore, these compounds are often more expensive than chloroquine itself and the concentrations required to reverse clinical drug-resistance for some of these agents can be toxic.

Accordingly, there is a need for safe, stable and inexpensive compositions and methods which reverse resistance to malarial quinoline.

SUMMARY OF THE INVENTION

This invention provides safe, stable and inexpensive compositions and methods which reverse resistance to malarial quinoline. The combination of a quinoline and a surfactant offers a treatment for malaria that:

1. is inexpensive for use in developing countries,
2. is comprised of two stable compounds that do not require expensive or unusual storage conditions,
3. provides increased absorption and decreased excretion of the anti-malarial component, and
4. does not require the introduction of other pharmacological agents with undesirable side effects.

It is an object of the invention to provide an agent that reverses quinoline resistance in *P. falciparum* malaria. Quinoline antimalarials include, but are not limited to, the 4 amino-quinolines (chloroquine, mefloquine, quinine, and quinidine) and the 8 amino-quinolines (primaquine and etaquine [WR238605])

According to a first aspect of the invention, a composition for reversing malarial resistance to quinoline antimalarials is provided. The composition comprises a synthetic, a natural or a hybrid surfactant in an admixture with a pharmaceutically acceptable carrier, excipient, or diluent. Preferably, the surfactant is the synthetic compound nonylphenolethoxylate ("NPE") having between 10 and 70 ethoxylate units.

According to a second aspect of the invention, a composition for the treatment or prevention of malaria is provided. The composition comprises a pharmaceutically effective amount of a quinoline in combination with a surfactant, the surfactant being adapted to reverse malarial resistance to the quinoline. Preferably, the surfactant is NPE having between 10 and 70 ethoxylate units.

According to a third aspect of the invention, a method of treating or preventing malaria is provided. The method comprises administering to a patient in need thereof one or both of the compositions described above.

According to a fourth aspect of the invention, a method of treating or preventing malaria is provided. The method comprises the steps of:

(a) forming a composition by combining a pharmaceutically effective amount of quinoline with a pharmaceutically effective amount of a surfactant; and (b) administering an effective dose of the composition to a patient infected with or at risk of contracting malaria.

Preferably, the surfactant is NPE having between 10 and 70 ethoxylate units.

Other objects, features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

In order that the invention may be more clearly understood, the preferred embodiments thereof will now be described in detail by way of example, with reference to the accompanying drawings, in which.

⊥$IC_{50}$ values represent the concentration at which 50% of the parasites present are killed or have their growth inhibited.

Figure 3:
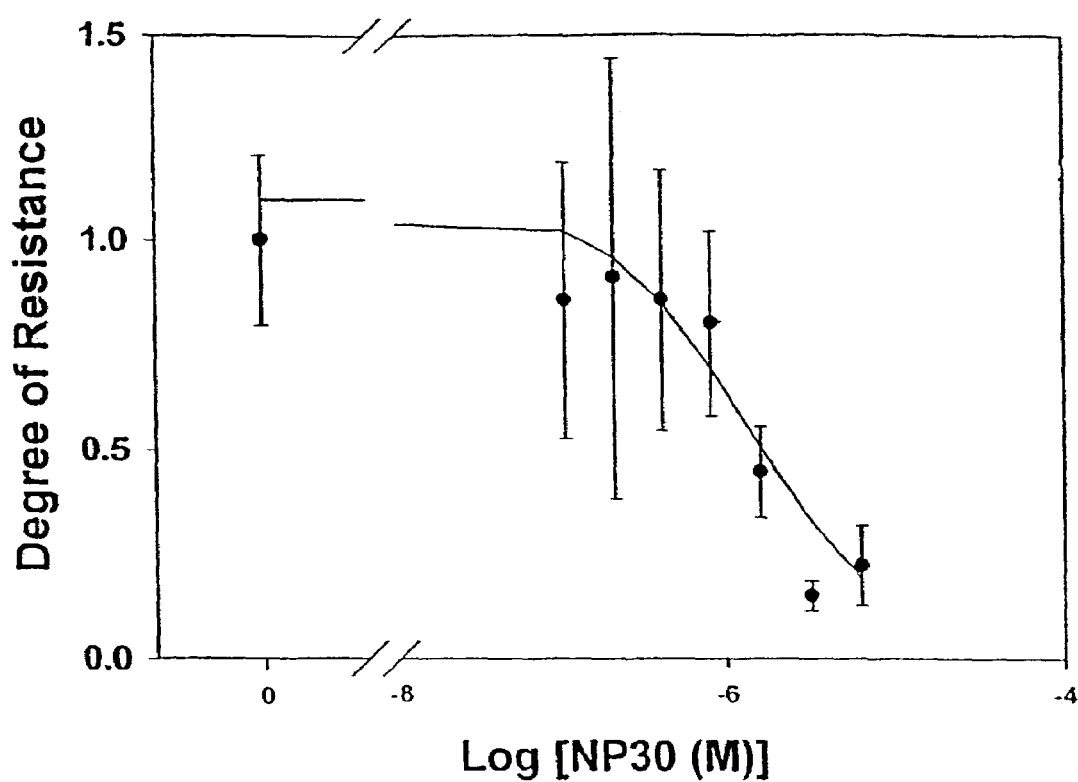

FIG. 3 shows the effect of adding increasing amounts of NP30 on the degree of chloroquine resistance of *P. falciparum*. The degree of chloroquine resistance is calculated as the $IC_{50}$ value observed in the presence of various concentrations of NP30 divided by the control (no NPE added) chloroquine $IC_{50}$ (274±56 nM). Values greater than 1 indicate that the particular NPE is rendering the *P. falciparum* parasites less sensitive to chloroquine, while values less that 1 indicate that the particular NPE is sensitizing the *P. falciparum* to chloroquine. Non-linear analysis of the data points indicates that a NP30 concentration of approximately 1 µM (0.0002% on a weight/volume basis) results in a 50% decrease in the degree of chloroquine resistance of the parasites.

DESCRIPTION OF THE PREFERRED EMBODIMENT

Although the description refers to nonylphenolethoxylate or NPE, as a preferred surfactant, such references are not intended to be limiting. It will be understood to those skilled in the art that natural surfactants, such as fatty acids, oils, bile acids, cholates, cholesterol esters, phospholipids, and chemically modified forms of these materials, as well as synthetic surfactants such as the Brij™ series, the Tween™ series, the octylphenol ethoxylate (OPE) Series, the NPE series and any of the synthetic surfactants such as those listed in "Industrial Surfactants" by Ernest W. Flick, Noyes Publications, Park Ridge, N.J. USA (1988) ISBN 0-8155-1173-6 may be used and are within the scope of this invention.

Figure 1:
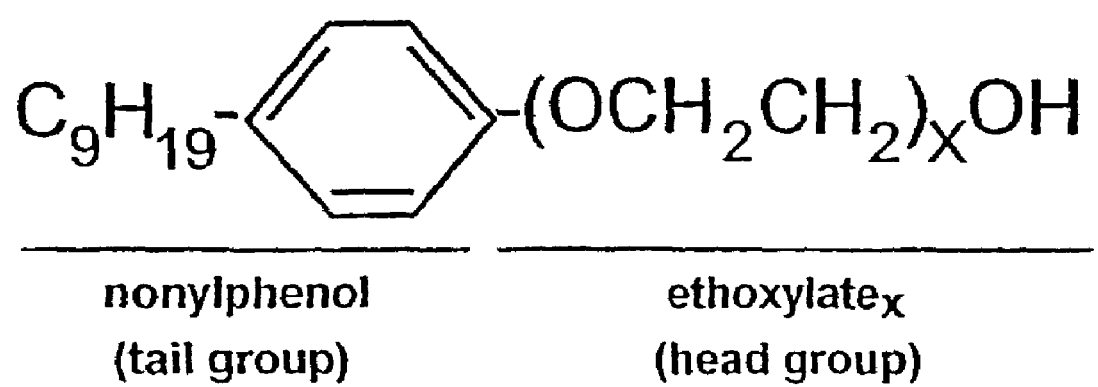
FIG. 1 shows the general chemical structure of nonylphenolethoxylates (NPEs).

As shown in FIG. 1, nonylphenolethoxylates (NPEs) consist of a hydrophobic tail group with a polymeric hydrophilic head portion consisting of repeating units of ethoxylate. NPEs are synthesized by co-polymerization of ethylene oxide with nonylphenol thereby producing a polydisperse mixture of head group lengths (X values) as described by Robert M. Weinheimer and Pierre T. Varineau in their 1998 book "Nonionic surfactants" Volume 72 of the Surfactant Science Series, edited by Nico M. van Os, published by Marcel Dekker, Inc. (New York) (ISBN 0-8247-9997-6).

Nonylphenolethoxylates [Charuk. 1998] (NPEs, FIG. 1) are synthetic surfactants that are inexpensive enough to used in a variety of household products. They can be used as wetting agents and have been tested as intestinal permeability enhancers to improve oral drug delivery [Swenson, 1994]. Their toxicology has been investigated [Larson, 1963; Finnegan, 1953] as has their absorption, distribution and excretion in humans and rodents [Swenson, 1994; Knaak, 1966]. NPEs are rapidly absorbed orally and topically and are actively excreted into the urine of healthy control subjects by kidney P-glycoprotein [Charuk, 1998]. We have determined that the nonylphenol (NP) series of ethoxylate (EO) containing surfactants reversed chloroquine resistance in both established laboratory lines of *P. falciparum* and patient isolates. Optimal chloroquine resistance reversal for *P. falciparum* in vitro was seen for NPEs with approximately 30 ethoxylate units, whereas maximal activity for reversing mammalian P-glycoprotein multidrug resistance occurs with NPEs of 9 ethoxylate units [Loe, 1993]. This finding indicates that NPEs can be directed to interact preferentially with the parasite simply by altering the number of ethoxylate units in the surfactant's structure.

Methods

*P. falciparum* cultures were grown in A+ blood obtained by venipuncture of volunteers. Cultures of the laboratory lines ItG and 3D7 [Dolan, 1993] and the patient isolates were maintained by the method of Trager and Jensen [Trager, 1976] using RPMI 1640 supplemented with 10% human serum and 50 µM hypoxanthine. Patient isolates were obtained from pre-treatment blood samples from patients enrolled in ongoing and ethically approved studies at the Tropical Disease Unit (TDU), University of Toronto [Kain, 1998b; Zhong, 1999]. In vitro drug susceptibility testing was performed using the WHO In Vitro Micro Test (Mark III) [1997]. The $IC_{50}$ values were determined using a non-linear regression analysis of the dose-response curve.

NPEs were obtained from Union Carbide and were extensively dried by lyophilizing before being made up as 1% (w/v) stock solutions in water.

Results

Figure 2:
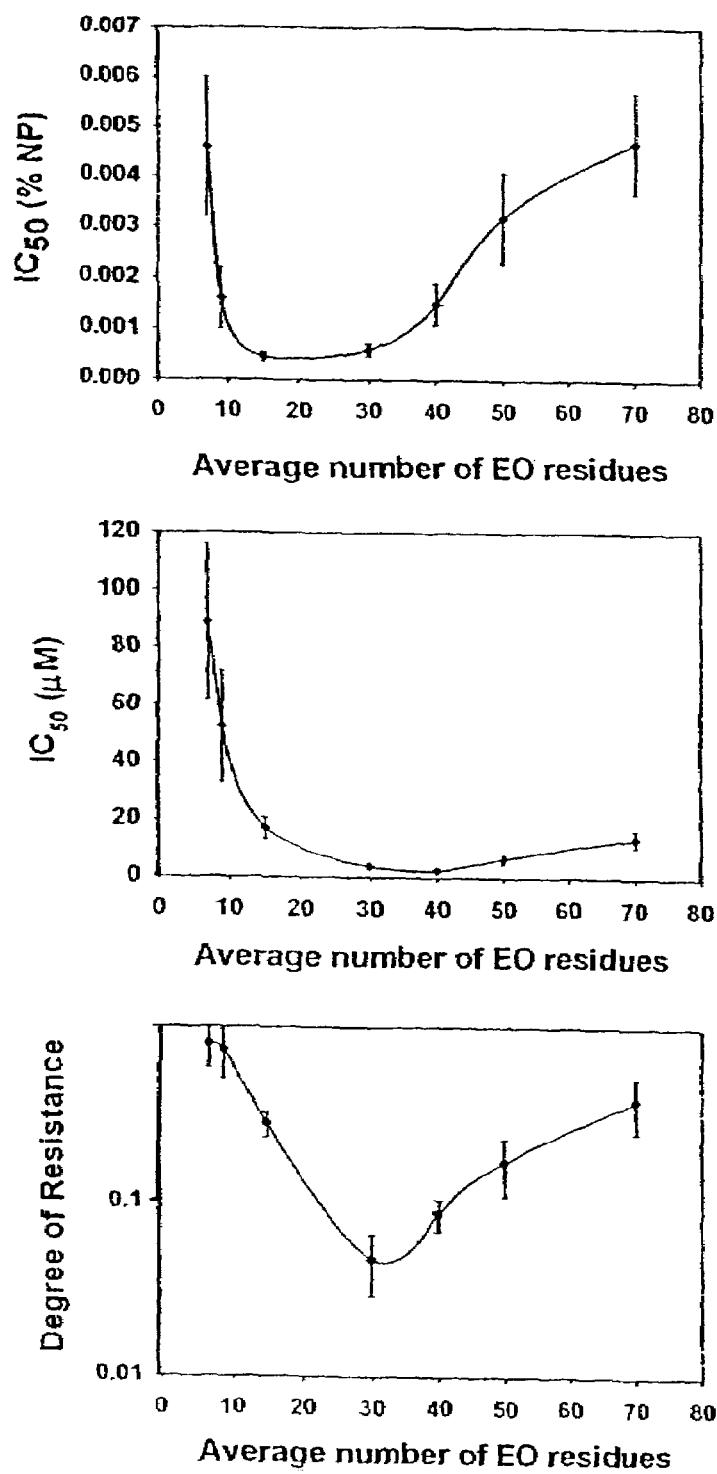
FIG. 2 shows anti-*P. falciparum* activity and sensitizing potential of NPEs. NPE solutions with increasing average EO content were tested for anti-*P. falciparum* activity and the $IC_{50}s$⊥ of these materials were determined using a non-linear regression analysis. $IC_{50}$ results are expressed on both a per weight basis (A, top panel) and on a molar concentration basis (B, middle panel). The ability of a 5 µM concentration of NPEs to sensitize *P. falciparum* in vitro to chloroquine was determined (C, bottom panel). The degree of chloroquine resistance is calculated as the $IC_{50}$ value observed in the presence of various NPEs divided by the control (no NPE added) chloroquine $IC_{50}$ (240±60 nM). Values greater than 1 indicate that the particular NPE is rendering the *P. falciparum* parasites less sensitive to chloroquine, while values less that 1 indicate that the particular NPE is sensitizing the *P. falciparum* to chloroquine. Anti-*P. falciparum* activity and sensitization are representative results obtained from multiple determinations. Results are plotted as mean with the standard error (as calculated by Sigma Plot) indicated with bars.

Initial experiments were undertaken to confirm that the parasite lines (e.g. 3D7) used for experimentation were chloroquine sensitive, or to examine the degree of chloroquine resistance present by determining the $IC_{50}$ for the ItG line, Isolate 1 and Isolate 2 (Table 1). We then proceeded to determine what effect increasing concentrations of surfactant alone had on each *P. falciparum* isolate in vitro. NPE preparations with a common hydrophobic tail group but with hydrophilic head groups of varying EO chain length were assayed for their direct activity against *P. falciparum*. On a per weight basis. NPEs with an average EO head length of >10 but <40 had the greatest anti-*P. falciparum* activity. When the results were corrected for the average molecular weights of the preparations it was observed that all NPEs with average EOs of >10 had low $IC_{50}$ values (FIG. 2B). The $IC_{50}$ values of these surfactants were significantly lower than the concentrations at which micelles form (>100 µM). The mechanism of action of NPEs is therefore unlikely to be simple disruption of membrane integrity. We then determined if NPEs were capable of reversing chloroquine resistance. Initial experiments indicated that 8 µM NP15 was able to reverse chloroquine resistance as effectively as 1 µM verapamil in the chloroquine resistant ItG line and two drug resistant patient isolates, one from India and one from Africa (Table 1). To determine if chloroquine sensitization was also dependent on the number of EO units in the head group of the surfactant, the reversal potential of the NPE series was determined using 5 µM concentrations of each surfactant. We determined that an NPE preparation with an average EO head length of 30 was the most effective chloroquine resistance reversal agent (FIG. 2C). To determine if both the tail and head groups were required for activity, the effect of the ethoxylate polymer polyethylene glycol (PEG, n~75), which has no tail group, was assayed. PEG was completely ineffective as a chloroquine sensitizing agent (Table 1) indicating that both the head and tail portions of NPE are required for reversal activity.

To determine what concentration of NP30 that was necessary to reverse chloroquine resistance to clinically achievable levels (~100 nM) the degree of chloroquine resistance was determined for several concentrations of NP30 (FIG. 3). The degree of chloroquine resistance is calculated as the $IC_{50}$ value observed in the presence of various concentrations of NP30 divided by the control (no NPE added) chloroquine $IC_{50}$ (274±56 nM). Values greater than 1 indicate that the particular NPE is rendering the *P. falciparum* parasites less sensitive to chloroquine, while values less that 1 indicate that the particular NPE is sensitizing the *P. falciparum* to chloroquine. Non-linear analysis of the data points indicates that a NP30 concentration approximately 1 µM (0.0002% on a weight/volume basis) results in a 50% decrease in the degree of chloroquine resistance of the parasites.

Discussion

The future use of NPEs as a malarial chloroquine resistance agents can be rationalized since unlike other reversal agents, they have weak, or no, pharmacological properties. Studies of NPE pharmacokinetics in mammals [Knaak, 1966] demonstrate that they are rapidly excreted. NPEs, particularly those with EO>10, are less toxic than shorter EO chain length surfactants (EO<10) [Finnegan, 1953]. Furthermore, NPEs represent a new class of *P. falciparum* sensitizing agents since they are uncharged molecules that do not have the requisite nitrogen atom in their structure [Bray, 1998]. Finally, NPEs are as stable and inexpensive as chloroquine itself, and therefore, their use in combination with chloroquine represents an inexpensive treatment or prevention option.

Treatment or prevention of malaria with a chloroquine/NPE combination provides at least three benefits:

1) NPEs enhance the gastrointestinal uptake of chloroquine [Swenson, 1994]. Varying the length of the head group of NPEs alters the hydrophobe/hydrophile balance of the surfactant, and while longer EO polymers may be less well absorbed they still facilitate intestinal absorption.

2) NPEs in the absence of a quinoline have antimalarial activity. Our results indicate that NPEs with longer head groups (those found in preparations with an average ethoxylate unit content of 30 units per nonylphenol group) inhibit the development of *P. falciparum* in red cells and therefore NPEs on their own function as anti-malarials.

3) While NPEs and chloroquine are antimalarial agents when used separately, in combination they have additive or synergistic effects that make them a potent anti-malarial combination. Further, since *P. falciparum* is sensitive to NPEs with head group lengths ≧15 EOs it is possible to treat or prevent *P. falciparum* infection with little, or no, effect on mammalian P-glycoprotein function. [Charuk, 1998].

The NPEs used in this study are a subset of the available head/tail group combinations that comprise commercially-available surfactants. Further separation of poly-disperse NPE preparations into compounds with uniform head group lengths may allow us to further define the optimal head length (EO number) that sensitizes chloroquine-resistant *P. falciparum*. An examination of other types of ethoxylate-containing surfactants will also allow us to determine which tail groups are most active. We believe that fatty acids, oils, bile acids, cholates, cholesterol esters, phospholipids, and chemically modified forms of these materials (such as Cremophor [Woodcock et al.], and Solutol H515 [Coon et al., Buckingham et al.]) as well as synthetic surfactants such as the Brij™ series, the Tween™ series, the OPE Series, the NPE series and any of the synthetic surfactants such as those listed in "Industrial Surfactants" [Ernest W. Flick, Noyes Publications, Park Ridge, N.J. USA (1988) ISBN 0-8155-1173-6] are promising malarial drug resistance reversal agents.

To design and obtain products that reverse malarial resistance to chloroquine we will systematically test a variety of commercially available surfactants. To assay for reversal activity, human red blood cells parasitized with *P. falciparum* will be placed in 96 well cell culture plates. The plate will contain a series of chloroquine concentrations (typically from 5,000 to 5 nM) and after 24 hrs the viability of the malaria will be determined using an assay that measures the levels of *Plasmodium* lactate dehydrogenase present [Mackler, 1993]. The data obtained from the enzyme assay will be analyzed using a non-linear curve fitting program (Sigma Plot—Jandel) and an $IC_{50}$ value will be derived. This process is repeated in the presence of putative surfactant sensitizing agents. The ability of a surfactant to sensitize *Plasmodium* to chloroquine or other quinolines is then expressed as the degree of resistance ($IC_{50}$ with agent/$IC_{50}$ without agent, where reversal of resistance gives values <1, increased resistance values >1, no effect values=1) [Oduola. 1998]. Using this assay we will evaluate surfactants with common tail groups, and then determine the effect of varying the head group (poly EO) on the compound's ability to sensitize *P. falciparum* to chloroquine and other quinolines. A wide variety of surfactants are commercially available, however they are usually polydisperse mixtures of single tail groups with a range of head group lengths that average to a stated value. These mixtures will be separated into their individual monodisperse constituents to allow us to determine the sensitization potential of individual surfactant species. The in vivo effect of surfactant sensitizing agents will be determined by infecting a cohort of *Aotus* monkeys with *P. falciparum* isolates with known quinoline resistance properties. One group of animals will be treated with a quinoline alone, a second will be treated with a surfactant preparation alone, and a third group will be treated with a quinoline in combination with a surfactant. The course of the infections will be followed and the efficacy of the quinoline/surfactant combination will be determined.

In view of the results described above, products containing natural, synthetic or hybrid surfactants in combination with quinolines, can be selected and designed in the manufacture of pharmaceutical compositions for the treatment or prevention of malaria. The pharmaceutical compositions can be administered to patients by methods known to those skilled in the art, such as oral capsule, aerosol administration, direct lavage and intravenous injection. Dosages to be administered depend on patient needs, on the desired effect and on the chosen route of administration.

The pharmaceutical compositions can be prepared by known methods for the preparation of pharmaceutically acceptable compositions which can be administered to patients, and such that an effective quantity of the products are combined in a mixture with a pharmaceutically acceptable vehicle. Suitable vehicles are described, for example in Remington's Pharmaceutical Sciences (Remington's Pharmaceutical Sciences, Mack Publishing Company, Easton, Pa., USA 1990).

On this basis, the pharmaceutical compositions could include one or more active ingredients, in association with one or more pharmaceutically acceptable vehicles, such as carriers, excipients or diluents, and contained in buffered solutions with a suitable pH and isoosmotic with the physiological fluids. The methods of combining suitable products with the vehicles is well known to those skilled in the art.

When used for parenteral administration, the pharmaceutical compositions of the present invention may be formulated in a variety of ways. Aqueous solutions having the composition of the present invention may be encapsulated in polymeric beads, liposomes, nanoparticles or other injectable depot formulations known to those of skill in the art. (Examples thereof may be found, for example, in Remington's Pharmaceutical Sciences, 18th Edition, 1990.)

Compositions including a liquid pharmaceutically inert carrier such as water may also be considered for both parenteral and oral administration. Other pharmaceutically compatible liquids may also be used. The use of such liquids is well known to those of skill in the art. (Examples thereof may be found, for example, in Remington's Pharmaceutical Sciences, 18th Edition, 1990.)

The dose level and schedule of administration may vary depending on the particular product used, the method of administration, and such factors as the age and condition of the patient.

Oral formulations of products may optionally and conveniently be used in compositions containing a pharmaceutically inert carrier, including conventional solid carriers, which are conveniently presented in tablet or capsule form. Formulations for rectal or transdermal use may contain a liquid carrier that may be oily, aqueous, emulsified or contain certain solvents suitable to the mode of administration. Suitable formulations are known to those of skill in the art. (Examples thereof may be found, for example, in Remington's Pharmaceutical Sciences, 18th Edition. 1990.)

Having illustrated and described the principles of the invention in a preferred embodiment, it should be appreciated to those skilled in the art that the invention can be modified in arrangement and detail without departure from such principles. All modifications coming within the scope of the following claims are claimed.

All publications, patents and patent applications referred to in this application are incorporated by reference in their entirety to the same extent as if each individual publication, patent or patent application was specifically and individually indicated to be incorporated by reference in its entirety.

REFERENCES

1. Basco L K, Le Bras J. In vitro activities of chloroquine in combination with chlorpromazine or prochlorperazine against isolates of *Plasmodium falciparum. Antimicrob Agents Chemother* 1992;36(1):209–13.
2. Basco L K, Le Bras J. In vitro reversal of chloroquine resistance with chlorpheniramine against African isolates of *Plasmodium falciparum. Jpn J Med Sci Biol* 1994;47 (1):59–63.
3. Bray P G, Ward S A. A comparison of the phenomenology and genetics of multidrug resistance in cancer cells and quinoline resistance in *Plasmodium falciparum. Pharmacol Ther* 1998;77(1):1–28.
4. Bray P G, Mungthin M. Ridley R G, Ward S A. Access to hematin: the basis of chloroquine resistance. *Mol Pharmacol* 1998:54(1):170–9.
5. Charuk J H, Grey A A, Reithmeier R A. Identification of the synthetic surfactant nonylphenol ethoxylate: a P-glycoprotein substrate in human urine. *Am J Physiol* 1998; 274(6):F1127–39.
6. Dolan S A, Herrfeldt J A, Wellems T E. Restriction polymorphisms and fingerprint patterns from an interspersed repetitive element of *Plasmodium falciparum* DNA. *Mol Biochem Parasitol* 1993;61(1): 137–42.
7. Finnegan J, Dienna J. Toxicological observations on certain surface-active agents. *Proceedings of the Science Section of the Toilet Goods Association* 1953;20:16–19.
8. Kain K C, Keystone J S. Malaria in travellers: Prevention and treatment. *Inf Dis Clinics of North Amer* 1998a; 2:2.1–18
9. Kain K C, Harrington M A, Tennyson S, Keystone J S. Imported malaria: prospective analysis of problems in diagnosis and management. *Clin Infect Dis* 1998b;27(1): 142–9.
10. Knaak. J. B., Eldridge, J. M., and Sullivan, L. J., "Excretion of certain polyethylene glycol ether adducts on nonylphenol by the rat. *Toxical. Appl. Pharmacol.* 9: 331–340, 1966
11. Larson P, Borzelleca J, Bowman E, Crawford E, Smith J, Hennigar G. Toxicological studies on a preparation of p-tertiary octylphenoxy-polyethyl ethanols (Triton X405). *Toxicology and Applied Pharmacology* 1963;5: 782–789.
12. Loe D W, Sharom F J. Interaction of multidrug-resistant Chinese hamster ovary cells with amphiphiles. *Br J Cancer* 1993;68(2):342–51.
13. Mackler M T, Ries J M, Williams J A. et al. Parasite lactate dehydrogenase as an assay for *Plasmodium falciparum* drug sensitivity. *Am J Trop Med Hyg* 1993;48(6), 739–41.
14. Marsh K. Malaria disaster in Africa. *Lancet* 1998;352 (9132):924.
15. Milhous W, Kyle D. Introduction to the Modes of Action of and Mechanisms of Resistance to Antimalarials. In: Sherman I W. ed. Malaria: Parasite Biology, Pathogenesis and Protection. Washington. D.C.: ASM Press, 1998: 303–316.
16. Martin S, Oduola A, Milhous W. Reversal of chloroquine resistance in *Plasmodium falciparum* by verapamil. *Science* 1987:235:899–901.
17. Oduola A M, Sowunmi A, Milhous W K, et al. In vitro and in vivo reversal of chloroquine resistance in *Plasmodium falciparum* with promethazine. *Am J Trop Med Hyg* 1998:58(5):625–9.
18. Su X, Kirkman L A, Fujioka H, Wellems T E. Complex polymorphisms in an approximately kDa protein are linked to chloroquine-resistant *P. falciparum* in Southeast Asia and Africa. *Cell* 1997;91(5):593–603.
19. Swenson E S, Milisen W B, Curatolo W. Intestinal permeability enhancement: structure-activity and structure-toxicity relationships for nonylphenoxypolyoxyethylene surfactant permeability enhancers. *Pharm Res* 1994:11(10):1501–4.
20. Trager W, Jensen J. Human malaria parasites in continuous culture. *Science* 1976;193:673–675.
21. White N J. Not much progress in treatment of cerebral malaria. *Lancet* 1998; 353(9128):594–5
22. WHO. In vitro micro-test (mark III) for the assessment of the response of *Plasmodium falciparum* to chloroquine, mefloquine, quinine, amodiaquine, sulfadoxine/pyrimethamine and arteminisinin: World Health Organization, 1997.
23. Zhong K J Y, Kain K C. Evaluation of a colorimetric PCR-based assay to diagnose *plasmodium falciparum* malaria in travelers. *J Clin Microbiol* 1999;37(2):339–41.

We claim:

1. A composition for reversing malarial resistance to a quinoline antimalarial agent comprising a quinoline antimalarial agent and a nonylphenolethoxylate (NPE) surfactant comprising 20 to 40 ethoxylate units, in an admixture with a pharmaceutically acceptable carrier, excipient, or diluent.

2. The composition of claim 1, wherein the quinoline antimalarial agent comprises a 4-amino quinoline, an 8-amino quinoline, halofantrine or mefloquine.

3. The composition of claim 1, wherein the NPE surfactant comprises NPE30.

4. The composition of claim 1, wherein the NPE surfactant on average contains 30 ethoxylate units.

5. A method of i) reducing the risk of a patient developing malaria if the patient is exposed to *Plasmodium* or, ii) treating malaria in a patient, comprising administering to the patient in need thereof, a composition as claimed in claim 1, 2, 3 or 4.

6. A method of treating malaria in a patient comprising the steps of:

(a) forming a composition by combining a pharmaceutically effective amount of a quinoline antimalarial agent with a pharmaceutically effective amount of a NPE surfactant comprising 20 to 40 ethoxylate units; and (b) administering an effective dose of the composition to the patient with malaria.

7. The method of claim 6, wherein the quinoline antimalarial agent comprises a 4-amino quinoline, an 8-amino quinoline, halofantrine or mefloquine.

8. The method of claim 6, where the NPE surfactant comprises NPE30.

9. The method of claim 6, wherein the NPE surfactant on average contains 30 ethoxylate units.

10. The composition of claim 1, comprising an oral composition or a parenterally injectable composition.

11. The composition of claim 2, wherein the 4-amino quinoline comprises chloroquine.

12. The composition of claim 2, wherein the quinoline antimalarial agent comprises mefloquine.

13. The method of claim 7, wherein the 4-amino quinoline comprises chloroquine.

14. The method of claim 7, wherein the quinoline antimalarial agent comprises mefloquine.

15. The method of claim 5, wherein the *Plasmodium* comprises *Plasmodium falciparum*.

16. A method of i) reducing the risk of a patient developing malaria if the patient is exposed to *Plasmodium* or, ii) treating malaria in a patient, comprising administering to the patient in need thereof, a composition as claimed in claim 1, 2, 3 or 4, wherein the patient in need thereof has been exposed to, or needs treatment for malaria caused by, quinoline anitimalarial agent-resistant *Plasmodium*.

* * * * *